United States Patent
Kim et al.

(10) Patent No.: US 10,195,149 B2
(45) Date of Patent: Feb. 5, 2019

(54) CONTINUOUS PROCESS FOR PREPARING MICROSPHERES AND MICROSPHERES PREPARED THEREBY

(71) Applicant: CJ HEALTHCARE CORPORATION, Seoul (KR)

(72) Inventors: Yi Mi Kim, Yongin-si (KR); Sun Kyung Lim, Yongin-si (KR); Mi Ran Park, Seoul (KR); Young Joon Park, Seoul (KR); Seung Hee Baek, Suwon-si (KR); Hyun Woo Shin, Seoul (KR)

(73) Assignee: CJ HEALTHCARE CORPORATION, Seoul (KR)

( * ) Notice: Subject to any disclaimer, the term of this patent is extended or adjusted under 35 U.S.C. 154(b) by 0 days.

(21) Appl. No.: 14/278,035

(22) Filed: May 15, 2014

(65) Prior Publication Data
US 2014/0341997 A1    Nov. 20, 2014

(30) Foreign Application Priority Data

May 15, 2013   (KR) ........................ 10-2013-0055356

(51) Int. Cl.
| | | |
|---|---|---|
| *A61K 9/16* | (2006.01) | |
| *A61K 38/22* | (2006.01) | |
| *B01F 3/08* | (2006.01) | |
| *B01F 5/04* | (2006.01) | |
| *B01F 15/02* | (2006.01) | |

(52) U.S. Cl.
CPC .......... *A61K 9/1682* (2013.01); *A61K 9/1647* (2013.01); *A61K 9/1694* (2013.01); *A61K 38/22* (2013.01); *B01F 3/0807* (2013.01); *B01F 5/04* (2013.01); *B01F 15/0222* (2013.01); *B01F 2215/0032* (2013.01)

(58) Field of Classification Search
None
See application file for complete search history.

(56) References Cited

U.S. PATENT DOCUMENTS

| | | |
|---|---|---|
| 4,652,441 A | 3/1987 | Okada et al. |
| 5,945,126 A | 8/1999 | Thanoo et al. |
| 2003/0003057 A1* | 1/2003 | Weers ................. A61K 9/0075 424/46 |
| 2011/0204533 A1* | 8/2011 | Winchester et al. .......... 264/4.6 |

FOREIGN PATENT DOCUMENTS

| | | | |
|---|---|---|---|
| CN | 1272058 A | 11/2000 | |
| JP | 2001-512461 A | 8/2001 | |
| KR | 1020100094227 A | 8/2010 | |
| WO | 98/35654 A1 | 8/1998 | |
| WO | WO-9916422 A1 * | 4/1999 | .......... A61K 9/0073 |
| WO | 01/36583 A1 | 5/2001 | |

OTHER PUBLICATIONS

Office Action for Chinese Patent Application No. 2014-10206674.7 (19 pages) with English translation, dated Mar. 14, 2017.

* cited by examiner

*Primary Examiner* — Jessica Worsham
(74) *Attorney, Agent, or Firm* — Seed IP Law Group LLP (57) ABSTRACT

The present invention relates to a continuous process for preparing microspheres and microspheres prepared thereby, and in particular, a process for preparing microspheres comprising steps of injecting a first emulsion and a second emulsion at the same time to form microspheres instantaneously, applying high pressure to the microspheres formed, and injecting the microspheres into an agitator, wherein the steps can be carried out continuously, and microspheres prepared thereby.

When microspheres are prepared using the method of the present invention, scale variables, which have been the biggest disadvantage in existing preparation methods of microspheres, can be significantly reduced, drug encapsulation efficiency can be improved, and small and uniform particles can be obtained.

12 Claims, 2 Drawing Sheets

CONTINUOUS PROCESS FOR PREPARING MICROSPHERES AND MICROSPHERES PREPARED THEREBY

FIELD OF THE INVENTION

The present invention relates to a continuous process for preparing microspheres and microspheres prepared thereby, and in particular, a process for preparing microspheres comprising steps of injecting a first emulsion and a second emulsion at the same time to form microspheres instantaneously, applying high pressure to the microspheres formed, and injecting the microspheres into an agitator, wherein the steps can be carried out continuously, and microspheres prepared thereby.

BACKGROUND ART

General methods for preparing microspheres normally include the steps of dissolving a biodegradable polymer carrier in a solvent, dissolving a water-soluble drug in the aqueous phase to form a first emulsion, and injecting the first emulsion into a second solution of poly(vinyl alcohol) (PVA) to form microspheres. This method is typically termed a discontinuous process. This discontinuous process is a method for preparing microspheres by injecting a first emulsion into one reactor that includes a second solution, and most commercialized processes fall under this type of discontinuous process.

Since Takeda Chemical Industries, Ltd. was granted the first patent (U.S. Pat. No. 4,652,441) relating to a discontinuous double emulsification method that led to mass production and commercialization, many related patent applications have been filed. However, such a discontinuous process produces microspheres having a very wide particle size distribution of approximately 1 to 400 µm, and has a high probability of the occurrence of microsphere aggregations or non-globular microspheres, and has difficulties in that the process parameters need to be controlled whenever increase of production scale is required for commercialization.

Poly(lactic-co-glycolic acid) (PLGA) or poly(lactic acid) (PLA), which is one of the most typical biodegradable polymer carriers, is water-insoluble and is very quickly precipitated when injected to an aqueous solution after being dissolved in an organic solvent. Using the above properties provides an advantage in that when a water-soluble drug and a polymer carrier are emulsified and then injected to a second solution, the polymer carrier can be quickly cured to form particles in which the drug can be encapsulated. However, there is a disadvantage in that the shape or the size of the particles is difficult to control since the particles are quickly cured. Particularly, when production scale and volume increase, the fast curing of particles is more difficult to control.

Generally, in order to control the fast curing of particles, a method of instantaneously applying high energy to a second emulsion by using means such as high-speed circulation of the second emulsion, homogenization, and ultrasonication, may be used. However, there are difficulties in increasing the energy to a sufficient amount in order to obtain uniform particles when the volume of the second emulsion increases proportionally with the increase of production scale.

In addition, when a second emulsion is prepared by injecting a first emulsion to one reactor to form particles, many parameters such as the injection time of the first emulsion, the temperature, the volume ratio of the first emulsion and a second aqueous solution, the concentration of a polymer carrier, the location to which the first emulsion is injected, whether the second emulsion is circulated or not, and the evaporation time of a solvent play important roles.

Therefore, increasing from a laboratory scale to a pilot or production scale is very difficult and is very often the biggest cause for failure. In addition, particles prepared by a discontinuous process have a large particle size distribution, and the size distribution also varies depending on the scale, therefore, the output of a specific preparation is not reproducible.

In view of the above, the inventors have completed the present invention by verifying that microspheres with a desired size such as a nano size can be reproducibly prepared by carrying out continuously the steps of injecting a first emulsion and a second emulsion simultaneously to form microspheres instantaneously, and applying high pressure to the above.

SUMMARY OF THE INVENTION

An object of the present invention is to provide a process for preparing microspheres, which can obtain excellent particle size distribution, can control the size of particles, and is suitable for mass production.

Another object of the present invention is to provide microspheres prepared by the said process.

Still another object of the present invention is to provide a drug delivery agent that includes the microspheres as an active component.

In order to solve the above problems, the present invention provides a process for preparing microspheres in which a physiologically active substance is encapsulated in a carrier polymer using a double emulsification method, the process comprising the steps of:

dispersing or mixing a carrier polymer and a physiologically active substance to form a first emulsion (Step 1);

continuously mixing a certain amount of each of the first emulsion and a second solution in which a surfactant is dissolved, to form a second emulsion (Step 2); and applying pressure to the second emulsion (Step 3).

Preferably, the process for preparing microspheres of the present invention may further include the step of stirring the second emulsion (Step 4) after Step 3.

The process for preparing microspheres of the present invention enables the mass production of microspheres of a desired size such as a nano size reproducibly by a continuous process since microspheres are instantaneously formed by bringing a certain amount of each of the first emulsion and the second solution in contact with each other continuously, and then the microspheres are subject to a high pressure process.

In addition, it is expected that the process for preparing microspheres of the present invention further increases the effect of minimizing the scale parameters due to a continuous process by continuously carrying out the stirring process.

Various methods have been developed as conventional technologies relating to methods for preparing microspheres. The most typical method among these is a double emulsification method, and the most typical preparation process of a double emulsification method is a discontinuous process. However, in case of conventional methods, the production of particles of a desired size with uniform particle distribution has been recognized as a very difficult technological challenge. For example, non-uniform particles having a size of 1 µm to 100 µm, or sometimes bigger, are produced in a discontinuous double emulsification process that is generally applied in mass production.

A method of applying energy by continuously circulating a second emulsion is generally applied in order to solve this particle nonuniformity problem, however, the increase of required energy with the increase of the production scale acts as a limitation in overcoming the problem. It is a greater problem when very large energy needs to be applied instantaneously as in the preparation of nano sized particles. Accordingly, methods for the preparation of nano sized particles by greatly increasing the concentration of a surfactant, or preparation of particles in the form of a micelle through polymer pegilation have been tried, however, it is difficult to use these methods to obtain microspheres of various target particle sizes from nano size to micro size in a mass production process where the control of parameters is difficult, since, in these conventional technologies, changes in one preparation condition affect other various parameters.

However, surprisingly, the present invention provides a process for preparing microspheres, wherein microspheres are instantaneously formed in a second emulsion, and then pressure is applied to the second emulsion, and thereby various particle sizes of nano size to micro size can be readily obtained with just a change of pressure.

Step 1 is a step of dispersing or mixing a carrier polymer and a physiologically active substance to form a first emulsion that includes a physiologically active substance and a carrier polymer.

The term "physiologically active substance" used in the present invention is a substance that enhances or suppresses the function of a living body in the course of life by organisms, that is, it refers to a substance that plays a role of adjusting abnormal conditions caused due to deficiency or excessive secretion of subatances involved in functional regulation in vivo.

In the present invention, the physiologically active substance may be any one or more selected from the group consisting of a luteinizing hormone-release hormone (LHRH) homologue, a peptide, and salts thereof. Specifically, as the physiologically active substance, goserelin, leuprolide acetate, triptorelin, buserelin, nafarelin and the like may be used as an agonist, and cetrorelix, argitide and the like may be used as an antagonist, among LHRH analogues. In addition to these, both water-soluble and water-insoluble drugs such as proteins, DNAs and chemical drugs may all be used without any limitation. In addition, the physiologically active substance may be used either alone or in combination of two or more substances.

In the present invention, a solvent for dissolving the physiologically active substance includes water, for example, but is not limited to water, and all solvents capable of dissolving drugs may be used.

The term "carrier polymer" used in the present invention means a polymer that plays a role of carrying a physiologically active substance in order to deliver the physiologically active substance.

In the present invention, common polymers may be used as the above carrier polymer. Preferably, the carrier polymer may include a biodegradable polymer. Specifically, the carrier polymer may be one or more selected from the group consisting of polyester such as polylactide (PLA), polyglycolide (PGA) and poly(lactide-co-glycolide) (PLGA), polyorthoester, polyanhydride, polyamino acid, polyacetal, polycyanoacrylate, polycaprolactone, polydioxanone, polyalkylene alkylate and the like, but is not limited thereto.

In the present invention, the types of the solvent used to dissolve the carrier polymer are not particularly limited. For example, in the present invention, the first emulsion may be prepared by dissolving the carrier polymer in any one or more solvents selected from the group consisting of methylene chloride, chloroform, acetonitrile, dimethyl sulfoxide, dimethylformamide and ethyl acetate, but the solvent is not limited thereto.

Step 2 is a step of continuously mixing a certain amount of each of the first emulsion and a second solution in which a surfactant is dissolved, to form a second emulsion.

The term "surfactant" used in the present invention means a material dissolved in a second solution, and is a material that plays a role of facilitating the formation of particles in a second emulsion.

Typically, a surfactant is added to facilitate the formation of particles in a second emulsion of a double emulsification method. The most representative example includes poly (vinyl alcohol) that is a non-ionic surfactant. However, it is not limited to poly(vinyl alcohol), and polysorbate, poloxamer, polyethylene glycol and the like may be used.

The term "second solution" used in the present invention means a material to be mixed with a first emulsion in order to form a second emulsion.

In the present invention, an aqueous medium may be used as a solvent that forms the second solution, that is, a solvent that dissolves a surfactant, and water may be included as a specific example. However, the solvent is not limited to water, and all solvents capable of dissolving physiologically active substances may be used.

In the present invention, Step 2 may be performed by continuously transferring a certain amount of each of the first emulsion and the second solution to a reactor, in which the second emulsion is to be formed, by a liquid transfer pump, and mixing the first emulsion and the second solution to form the second emulsion.

In the present invention, the reactor may have a mesh net installed on the inside, and the second emulsion is formed after the first emulsion and the second solution pass through the mesh net.

In the present invention, the mesh net may have a pore size ranging from 0.1 µm to 10 mm, and preferably from 1 µm to 50 µm.

Step 3 is a step of applying pressure to the second emulsion, that is, a step that controls the particle size, particle size distribution, and the like, of microspheres by applying constant pressure to the second emulsion.

In the present invention, the pressure may range from 0 psi to 30,000 psi, preferably range from 500 psi to 30,000 psi, and more preferably range from 500 psi to 25,000 psi.

In the present invention, Step 3 may be performed by applying pressure using an apparatus that can apply high pressure such as a high pressure homogenizer or a high pressure pump.

In a microsphere preparation process, a high pressure process is generally used for the purpose of enhancing the efficiency of homogeneous mixing through high pressure homogenization when emulsion is formed. In particular, a high pressure homogenizer is typically used to achieve this purpose, however, a high pressure homogenizer is not actually applied in a commercial production of microspheres, and the preparation of microspheres using a high pressure homogenization process is not easy as well. In order to form fine particles using a common high pressure homogenizer, a second emulsion needs to be injected to an injection unit of a high pressure homogenizer and consecutively passes through a high pressure cell after the second emulsion is formed by mixing a first emulsion with a second solution. The rate of the second emulsion passing through the high pressure cell by the high pressure homogenizer is approximately an average of 70 mL/min, and the time required depends on the rate, and it takes longer as the preparation scale increases. Meanwhile, in the second emulsion of the injection unit, the polymer is cured as the solvent of the first emulsion is discharged, and non-uniform polymer aggregation and phase separation occur, and as a result, the formation of particles becomes impossible. Particularly, when using a hydrophobic polymer such as PLGA, and water as a second solvent, the rate of curing rapidly increases, and as a result, no particles are formed and a phenomenon in which the aggregates block the high pressure cell occurs as well.

In the present invention, (i) a second emulsion is instantaneously formed, and then (ii) the second emulsion passes through a high pressure process before the first emulsion is evaporated, which is different from typical high pressure processes, and as a result, a phenomenon in which microspheres are not formed due to the curing of a polymer during a high pressure process or the phase separation of emulsion, can be prevented.

Figure 1A:
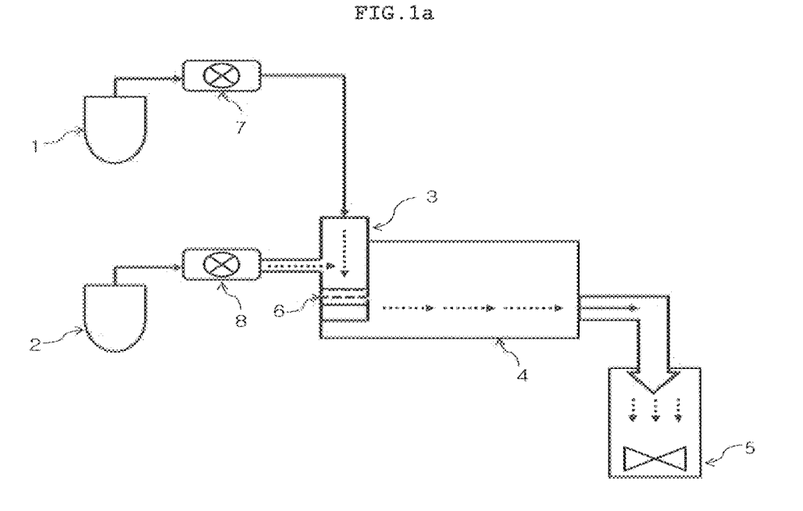
Figure 1B:
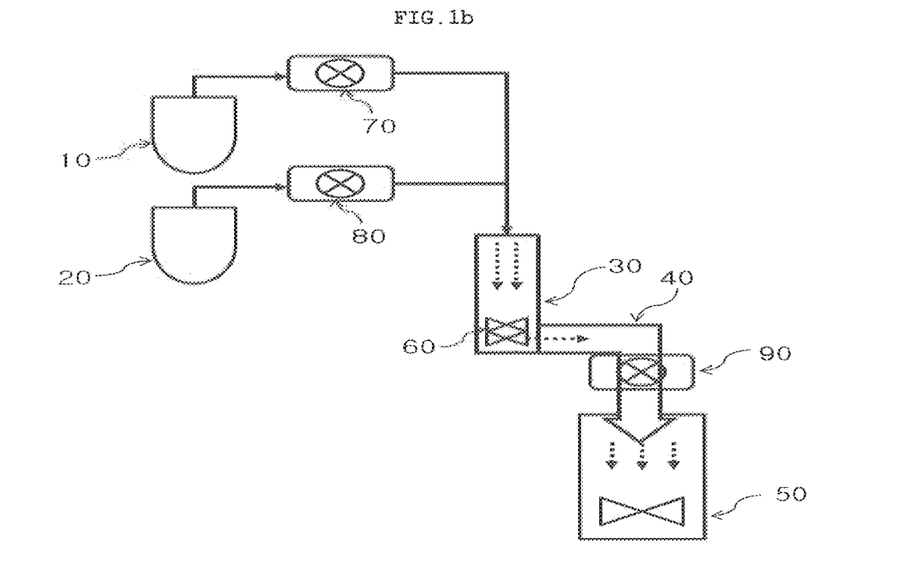

In the continuous process according to the present invention, the step of instantaneously forming a second emulsion and microspheres may be endlessly repeated, therefore, the process may be readily applied to mass production. In other words, in the present invention, a mesh net may be installed in a site (reactor unit) in which a first emulsion and a second solution are encountered and reacted, for example, an injection unit of a high pressure homogenizer, and microspheres may be formed instantaneously while the first emulsion and the second solution are pumped by a pump inside a high pressure homogenizer, and pass through the mesh net the moment the first emulsion is dripped to the mesh net (FIG. 1a). Alternatively, microspheres may be instantaneously formed by adjusting the encounter rate of a first emulsion and a second solution by a homogenizer installed instead of a mesh net (FIG. 1b).

There are related prior arts that adopt the concept of a continuous process, however, they have merely carried out continuously the process of forming particles and transferring the particles to a stirrer, and there are no prior arts that can obtain microspheres of up to nano sizes reproducibly as in the present invention.

Step 4 is a step of stirring the second emulsion, that is, a step that facilitates the formation of microspheres with uniform particle distribution by stirring the second emulsion at a constant rate.

In the present invention, Step 4 may be performed by continuously injecting the second emulsion from a reactor, in which the second emulsion is to be formed, to an agitator, and stirring the second emulsion in the agitator.

In the present invention, the rate of injecting the second emulsion to the agitator is preferably controlled to be the same as the rate of supplying the first emulsion and the second solution to the reactor.

In the present invention, means to inject the second emulsion to the agitator may include a high pressure pump or a liquid transfer pump, but is not limited thereto.

In addition, the present invention provides microspheres in which a physiologically active substance is encapsulated in the carrier polymer, prepared using the method described above.

Furthermore, the present invention provides a drug delivery agent that includes the microspheres as an active component.

In the present invention, the drug delivery agent may be in the form of an injection, but is not limited thereto.

In addition, the present invention provides an apparatus for preparing microspheres in which a physiologically active substance is encapsulated in a carrier polymer using a double emulsification method, the apparatus comprising:

a) a first container for holding a first emulsion in which a carrier polymer and a physiologically active substance are dispersed or mixed;

b) a second container for holding a second solution in which a surfactant is dissolved;

c) a reactor unit in which a second emulsion is formed by continuously injecting the first emulsion of the first container and the second solution of the second container;

d) a pressure unit for applying pressure to the second emulsion; and e) an agitator for stirring the solution passed through the pressure unit.

In the present invention, the pressure unit may include a high pressure homogenizer or a high pressure pump.

One embodiment of an apparatus for preparing microspheres by a continuous process according to the present invention is schematized in FIG. 1a, and another embodiment is schematized in FIG. 1b.

FIG. 1a simply shows an apparatus for preparing microspheres in which a second solution is supplied simultaneously as a first emulsion is dripped to the second solution and then passes through a mesh net thereby forming microspheres.

According to FIG. 1a, the apparatus for preparing microspheres of the present invention includes a first container (1) for holding a first emulsion in which a carrier polymer and a physiologically active substance are dispersed or mixed, a second container (2) for holding a second solution in which a surfactant is dissolved, a reactor unit (3) in which a second emulsion is formed by continuously injecting the first emulsion of the first container and the second solution of the second container, a pressure unit (4) for applying pressure to the second emulsion, and an agitator (5) for stirring the solution passed through the pressure unit (4). Herein, the pressure unit (4) may include a high pressure homogenizer equipped with a high pressure cell inside. In addition, pumps (7, 8) are used in order to transfer the first emulsion and the second solution, respectively, to the reactor unit.

At this time, when the second solution is supplied with a flow rate of 0.001 mL/min to 100 mL/min, preferably 1 mL/min to 50 mL/min, and more preferably 2 mL/min to 30 mL/min, the first emulsion is dripped in the reactor unit (3). The volume of a drip may range from approximately 0.01 µl to 100 ml, preferably range from 0.1 µl to 1 mL, and more preferably range from 20 µl to 100 µl. If the volume of the drip is smaller than 0.01 µl, there is a disadvantage in that the preparation volume becomes too big since the amount of the drip is too small.

Although not absolutely required, a mesh net (6) may be installed inside the reactor unit (3) in order to facilitate the formation of particles. At this time, the mesh net preferably has a pore size ranging from 0.1 µm to 10 mm. The pore size of a mesh net is one of the variables that determine the shape and the size of particles, and if the size is 0.1 µm or less, it is difficult for a liquid to pass through. The size of particles may be controlled according to the number of mesh nets, and the number of mesh nets preferably ranges from 1 to 10, however, the number is not particularly limited even though it is difficult for a liquid to pass through if the number of mesh nets is 10 or more. The material of a mesh net is also one of the important variables that determine the shape of the particles. For quick curing, the material of a mesh net is preferably stainless steel that has hydrophilicity, and for appropriately forming the shape of spheres, the material of a mesh net is preferably teflon or nylon. However, the material of a mesh net is not particularly limited.

The pressure of a high pressure homogenizer may range from 0 psi to 30,000 psi. 30,000 psi is only specified because of the mechanical limit of commercially available high pressure homogenizers, therefore, the pressure value that can be applied in the present invention is not limited thereto. Depending on the pressure of a high pressure homogenizer, the size of the particles may be diversely controlled from nano size (up to 500 nm) to micro size (20 to 30 µm). The pressure may be more preferably set to 0 psi to 25,000 psi in order to obtain round particles.

Depending on manufacturing facilities, the second emulsion may be transferred to a high pressure homogenizer after dripping the first emulsion and forming the second emulsion in a separate reactor installed outside the high pressure homogenizer instead of going through a high pressure cell after dripping the first emulsion to the second solution inside a high pressure homogenizer. In this case, the mesh net may be installed within a separate reactor installed outside the high pressure homogenizer.

Means to inject the second emulsion to an agitator is a high pressure pump or a liquid transfer pump.

FIG. 1b simply shows another embodiment of an apparatus for preparing microspheres according to the present invention.

According to FIG. 1b, an apparatus for preparing microspheres of the present invention includes a first container (10) for holding a first emulsion in which a carrier polymer and a physiologically active substance are dispersed or mixed, a second container (20) for holding a second solution in which a surfactant is dissolved, a reactor unit (30) in which a second emulsion is formed by continuously injecting the first emulsion of the first container and the second solution of the second container, a pressure unit (40) for applying pressure to the second emulsion, and an agitator (50) for stirring the solution passed through the pressure unit. A homogenizer (60) is installed inside the reactor unit (30). In addition, liquid transfer pumps (70, 80) may be used in order to transfer the first emulsion and the second solution, respectively, to the reactor unit, however, any means commonly used to transfer a liquid in the related arts may be appropriately selected and used by the judgment of those skilled in the related arts. The pressure unit (40) may include a high pressure pump (90), and in this case, the high pressure pump (90) applies pressure to the solution and transfers the solution to an agitator at the same time.

In other words, in FIG. 1b, when the second solution is supplied to the reactor unit (30) attached with the homogenizer (60) using the liquid transfer pump (80), and the first emulsion is supplied to the reactor unit (30) attached with the homogenizer (60) using the liquid transfer pump (70), the homogenizer (60) forms microspheres instantaneously. The formed microspheres are transferred to the agitator (50) at a constant rate by the pressure applied by the high pressure pump (90).

The particles, which are formed non-uniformly in large sizes when the second emulsion is formed, are formed uniformly in very small sizes by the instantaneous energy applied by the pressure of the high pressure pump (90). The higher the instantaneous energy applied by the high pressure pump (90), the smaller the formed particles as the particles are decomposed by a strong pulse. In other words, the high pressure pump (90) in the present invention is not only liquid transfer means but also is effective in forming the particles uniformly in very small sizes by instantaneous energy.

The rate of the solution transferred to an agitator decreases as the pressure of the high pressure pump decreases. When the pressure of the high pressure pump is set to 25,000 psi in one embodiment of the present invention, the solution was transferred at a rate of 70 mL/min. As the pressure decreases, the time required for the preparation increases since the transfer rate of the solution decreases, and as the pressure increases, the time required for the preparation decreases since the transfer rate of the solution increases.

The rate of transferring the second solution using a liquid transfer pump and the rate of transferring the first emulsion need to be appropriately adjusted, and the rate of transferring the formed microspheres to an agitator and the rate of supplying the second solution need to be similar in order to form the second emulsion having a constant volume at all times in the reactor unit (30). The transfer rate of microspheres to an agitator ranges from approximately 1 mL/min to 100 mL/min, and preferably ranges from 20 mL/min to 70 mL/min, however, the rate is not particularly limited. As the preparation scale increases, the transfer rate may be set to be fast for the reduction of time taken. When microspheres are continuously formed while a constant volume is maintained in a specific container, the only variable depending on the change of preparation volume in obtaining microspheres of certain sizes is time. The preparation time increases in proportion to the increase of preparation scale.

Advantageous Effects

The present invention provides a method for preparing microspheres in which constant amounts of microspheres are continuously produced. In the present invention, when compared to the preparation of particles using typical discontinuous processes, it is possible to prepare particles that are small and uniform despite the increase of a preparation volume, and there is no need to change containers or preparation conditions even when the preparation volume increases. There is an advantage in that particle forming conditions are maintained constantly at all times through the process of continuously forming and transferring the second emulsion in a constant volume.

Greater absolute quantities of microspheres that satisfy a desired condition can be secured as the preparation volume increases, since the preparation volume can be increased without limit by just proportionally increasing the time while the particle forming conditions are maintained constantly. In other words, it is effective in that the uniformity of particles is improved as the preparation volume increases.

In addition, according to the present invention, there is an advantage in that the size of particles can be readily adjusted to a target level such as nano size or micro size by adjusting the pressure applied during the particle forming processes, and the shape and the encapsulation efficiency of the particles may be determined depending on the material and the number of mesh nets, and the pore size of mesh nets.

Furthermore, in a discontinuous process, a highly viscous first emulsion is injected to a second solution for high-content encapsulation, however, it is difficult to inject a highly viscous first emulsion due to the high shearing force when injected, and 0.2 µm sterilized filtering is not possible as well. However, in the present invention, a highly viscous first emulsion is not required since microspheres are formed instantaneously, and high-content encapsulation is possible even at the concentration that 0.2 μm sterilized filtering is possible.

BRIEF DESCRIPTION OF THE DRAWINGS

FIGS. 1a and 1b simply schematize an apparatus for a continuous process of the present invention for forming microspheres. Herein, FIG. 1a schematizes a manufacturing apparatus in which a second solution is injected at a constant rate using a liquid transfer pump when a first emulsion is dripped, a second emulsion is formed while the first emulsion and the second solution pass through a mesh net, homogeneous particles are formed as this second emulsion passes through a high pressure homogenizer that is a pressure unit, and the second emulsion is continuously injected to an agitator. In addition, FIG. 1b schematizes a manufacturing apparatus in which, when a second solution is supplied to a reactor unit equipped with a homogenizer through a liquid transfer pump, and a first emulsion is supplied to the reactor unit equipped with the homogenizer using the liquid transfer pump, the homogenizer instantaneously forms microspheres, and the formed microspheres are transferred to an agitator after passing through a high pressure pump.

FIG. 2a shows the microspheres prepared according to Example 4 with a preparation scale of 1 g, and FIG. 2b shows the microspheres prepared according to Example 5 with a preparation scale of 10 g.

DETAILED DESCRIPTION OF THE EMBODIMENTS

Hereinafter, the constitutions and the effects of the present invention are described more specifically with reference to examples, however, these examples are for illustrative purposes only, and the scope of the present invention is not limited to these examples.

EXAMPLE

In Examples 1 to 3, microspheres are prepared according to the process of FIG. 1a, and in Examples 4 and 5, microspheres are prepared according to the process of FIG. 1b.

Example 1: Preparation of Leuprolide Acetate-Containing Microspheres Using High Pressure Homogenizer Pressure of 5,000 psi 180 mg of leuprolide acetate was dissolved in 300 μl of distilled water, and 720 mg of PLGA (Resomer RG502H) was dissolved in 3 mL of methylene chloride. This polymer solution and a leuprolide acetate solution were mixed using a homogenizer, to prepare a first emulsion. After the prepared first emulsion was injected into a 10 mL syringe and the syringe was installed in a syringe pump, the first emulsion was dripped to the injection unit of a high pressure homogenizer at a rate of 0.6 mL/min. As a second solution, a solution containing 1% polyvinyl alcohol (molecular weight 30,000 to 50,000) in distilled water was also injected continuously thereto at a similar rate to the rate of the pump of the high pressure homogenizer transferring a liquid. The pressure of the high pressure homogenizer was 5,000 psi, and an average flow rate at the time was approximately 70 mL/min. The microspheres continuously formed through the high pressure pump of the high pressure homogenizer were injected to an agitator, and were stirred at an average of 100 to 150 rpm at room temperature. The microspheres prepared after the stirring of 4 hours were washed several times with distilled water and then were freeze-dried.

Example 2: Preparation of Leuprolide Acetate-Containing Microspheres Using High Pressure Homogenizer Pressure of 1,000 psi 180 mg of leuprolide acetate was dissolved in 300 μl of distilled water, and 720 mg of PLGA (Resomer RG502H) was dissolved in 3 mL of methylene chloride. This polymer solution and a leuprolide acetate solution were mixed using a homogenizer, and a first emulsion was prepared. After the prepared first emulsion was injected into a 10 mL syringe and the syringe was installed in a syringe pump, the first emulsion was dripped to the injection unit of a high pressure homogenizer at a rate of 0.6 mL/min. As a second solution, a distilled water solution containing 1% polyvinyl alcohol (molecular weight 30,000 to 50,000) was also injected continuously thereto at a similar rate to the rate of the pump of the high pressure homogenizer transferring a liquid. The pressure of the high pressure homogenizer was 1,000 psi, and an average flow rate at the time was approximately 20 to 30 mL/min. The microspheres continuously formed through the high pressure pump of the high pressure homogenizer were injected to a stirrer, and were stirred at an average of 100 to 150 rpm at room temperature. The microspheres prepared after the stirring of 4 hours were washed several times with distilled water and then were freeze-dried.

Example 3: Preparation of Leuprolide Acetate-Containing Microspheres Using High Pressure Homogenizer Pressure of 0 psi 180 mg of leuprolide acetate was dissolved in 300 μl of distilled water, and 720 mg of PLGA (Resomer RG502H) was dissolved in 3 mL of methylene chloride. This polymer solution and a leuprolide acetate solution were mixed using a homogenizer, and a first emulsion was prepared. After the prepared first emulsion was injected into a 10 mL syringe and the syringe was installed in a syringe pump, the first emulsion was dripped to the injection unit of a high pressure homogenizer at a rate of 0.6 mL/min. As a second solution, a distilled water solution containing 1% polyvinyl alcohol (molecular weight 30,000 to 50,000) was also injected continuously thereto at a similar rate to the rate of the pump of the high pressure homogenizer transferring a liquid. The pressure of the high pressure homogenizer was 0 psi, and an average flow rate at the time was approximately to 30 mL/min. The microspheres continuously formed through the high pressure pump of the high pressure homogenizer were injected to a stirrer, and were stirred at an average of 100 to 150 rpm at room temperature. The microspheres prepared after the stirring of 4 hours were washed several times with distilled water and then were freeze-dried.

Example 4: Method for Preparing Leuprolide Acetate-Containing Microspheres in Preparation Scale of 1 g 125 mg of leuprolide acetate was dissolved in 300 μl of distilled water, and 840 mg of PLGA (Resomer RG502H) was dissolved in 3 mL of methylene chloride. A first emulsion was prepared by homogenizing the leuprolide solution and the PLGA polymer solution using a homogenizer. The prepared first emulsion was injected to the injection unit of a reactor by being transferred at a flow rate of 3.3 mL/min using a liquid transfer pump. As a second solution, a distilled water solution containing 1% polyvinyl alcohol (molecular weight 30,000 to 50,000) was also injected to the injection unit of the reactor at a flow rate of 70 mL/min using a liquid transfer pump. A second emulsion was formed in the injection unit of the reactor by homogenizing the first emulsion and the second solution at an average of 20,000 rpm using a homogenizer installed on the inside in advance. The formed second emulsion was transferred to a stirrer through a transfer pipe. Inside the transfer pipe, a high pressure pump set to 25,000 psi was installed, and the second emulsion was injected to a stirrer at an average rate of 70 mL/min. The injection rate to the stirrer was adjusted to the same or a similar level to the injection rate of the second solution when the microspheres were formed. The microspheres injected to the stirrer were stirred at an average of 100 to 150 rpm for 4 hours at room temperature, were washed several times with distilled water, and then were freeze-dried.

Example 5: Method for Preparing Leuprolide Acetate-Containing Microspheres in Preparation Scale of 10 g 1.25 g of leuprolide acetate was dissolved in 3 mL of distilled water, and 8.4 g of PLGA (Resomer RG502H) was dissolved in 30 mL of methylene chloride. A first emulsion was prepared by homogenizing the leuprolide solution and the PLGA polymer solution using a homogenizer. The prepared first emulsion was injected to the injection unit of a reactor by being transferred at a flow rate of 3.3 mL/min using a liquid transfer pump. As a second solution, a distilled water solution containing 1% polyvinyl alcohol (molecular weight 30,000 to 50,000) was also injected to the injection unit of the reactor at a flow rate of 70 mL/min using a liquid transfer pump. A second emulsion was formed in the injection unit of the reactor by homogenizing the first emulsion and the second solution at an average of 20,000 rpm using a homogenizer that was installed on the inside in advance. The formed second emulsion was transferred to a stirrer through a transfer pipe. Inside the transfer pipe, a high pressure pump set to 25,000 psi was installed, and the second emulsion was injected to a stirrer at an average rate of 70 mL/min. The injection rate to the stirrer was adjusted to the same or a similar level to the injection rate of the second solution when the microspheres were formed. The microspheres injected to the stirrer were stirred at an average of 100 to 150 rpm for 4 hours at room temperature, were washed several times with distilled water, and then were freeze-dried.

Comparative Example 1: Preparation of Leuprolide Acetate-Containing Microspheres Using Conventional Double Emulsification Method A first emulsion was prepared by dissolving 50 mg of leuprolide acetate in 100 μl of distilled water and then mixing this solution to a polymer solution in which 450 mg of PLGA (Lakeshore 7525DLPLG2A) is dissolved in 1 mL of methylene chloride. The prepared first emulsion was dispersed to 200 mL of a distilled water solution containing 1% polyvinyl alcohol (molecular weight 30,000 to 50,000) prepared in advance using a homogenizer. A second emulsion was formed and then stirred for 2 hours, and the solvent was removed. The solidified microspheres were washed several times with distilled water and then were freeze-dried.

Comparative Example 2: Preparation of Leuprolide Acetate-Containing Microspheres Using Conventional Double Emulsification Method A first emulsion was prepared by dissolving 100 mg of leuprolide acetate in 100 μl of distilled water and then mixing this solution to a polymer solution in which 900 mg of PLGA (Lakeshore 7525DLPLG2A) is dissolved in 1 mL of methylene chloride. The prepared first emulsion was dispersed to 350 mL of a distilled water solution containing 1% polyvinyl alcohol (molecular weight 30,000 to 50,000) prepared in advance using a homogenizer. A second emulsion was formed and then stirred for 2 hours, and the solvent was removed. The solidified microspheres were washed several times with distilled water and then were freeze-dried.

Total preparation volume and time taken for particle preparation are shown in the following Table 1 when the preparation was carried out according to Examples 1 to 5, and Comparative Examples 1 and 2 of the present invention.

TABLE 1

| Classification | PLGA Conc. (mg/mL) | API Addition Amount (% by weight) | Production Scale (g) | Surfactant Included in Second Solution | Volume of Second Solution (mL) | Pressure (psi) | Time for Particle Preparation (min) |
|---|---|---|---|---|---|---|---|
| Example 1 | 240 | 10 | 1 | poly(vinyl alcohol) | 400 | 5,000 (High Pressure Homogenizer) | 10 |
| Example 2 | 240 | 10 | 1 | poly(vinyl alcohol) | 400 | 1,000 (High Pressure Homogenizer) | 10 |
| Example 3 | 240 | 10 | 1 | poly(vinyl alcohol) | 500 | 0 | 10 |
| Example 4 | 280 | 10 | 1 | poly(vinyl alcohol) | 150 | 25,000 (High Pressure Pump) | 2 |
| Example 5 | 280 | 10 | 10 | poly(vinyl alcohol) | 1500 | 25,000 (High Pressure Pump) | 15 |

TABLE 1-continued

| Classification | PLGA Conc. (mg/mL) | API Addition Amount (% by weight) | Production Scale (g) | Surfactant Included in Second Solution | Volume of Second Solution (mL) | Pressure (psi) | Time for Particle Preparation (min) |
|---|---|---|---|---|---|---|---|
| Comparative Example 1 | 450 | 10 | 0.5 | poly(vinyl alcohol) | 200 | — | 5 |
| Comparative Example 2 | 900 | 10 | 1 | poly(vinyl alcohol) | 350 | — | 5 |

Experimental Example 1: Measurement of Leuprolide Acetate Encapsulation Efficiency in Microspheres For the drug encapsulation efficiency, a constant amount of microspheres were used as a test liquid after being completely dissolved in dimethyl sulfoxide (DMSO) and filtered using a syringe filter, and the content of drugs encapsulated inside the microspheres was measured using HPLC. At this time, C18 column (150 mm L.×4.6 mm I.D. 5 μm) and Gemini-NX C18 column (4.0 mm L.×3.0 mm I.D.) were used for an HPLC analysis. The solvent and the mobile phase of the sample were potassium carbonate and 25% acetonitrile (ACN) aqueous solution (pH 7.0), and the sample was detected at UV 220 nm.

The content of the drug in the prepared microspheres was measured and the encapsulated amount was shown in the following Table 2.

TABLE 2

| Classification | Encapsulation Amount of Drug (Drug Weight/Total Particle Weight %) |
|---|---|
| Example 1 | 12 |
| Example 2 | 12 |
| Example 3 | 12 |
| Example 4 | 10 |
| Example 5 | 10 |
| Comparative Example 1 | 9.9 |
| Comparative Example 2 | 4.5 |

As is seen from Table 2, in most microsphere formulations, the drug encapsulated amount was 10 to 12% by weight, therefore, it was seen that the encapsulated amount was significantly improved when compared to the result of Comparative Example 1 that has a high polymer carrier concentration. The concentration of a polymer carrier is an important factor in determining an encapsulated amount, and in existing microsphere preparation methods, the concentration of a polymer carrier needs to be high, that is, 800 to 900 mg/mL, in order to reach an encapsulated amount of 10%. However, a highly concentrated polymer carrier solution has high viscosity thereby has very high shearing force when being injected to a second solution after the formation of a first emulsion. In addition, there is a disadvantage in that sterilized filtering is impossible when the viscosity is high. The present invention has an advantage in that the encapsulated amount may increase to 10 to 12% even at 240 to 320 mg/mL, which is a low polymer carrier concentration.

Experimental Example 2: Measurement of Leuprolide Acetate-Containing Microsphere Particle Size The particle size of microspheres was measured by redispersing the freeze-dried particles to a water phase using a wet particle size analyzer (Mastersize 2000S, Malvern, USA).

The results are shown in the following Table 3.

TABLE 3

| | Particle Distribution | | | Average Particle |
|---|---|---|---|---|
| Classification | D(0.1) | D(0.5) | D(0.9) | Size (μm) |
| Example 1 | 1.6 | 3.8 | 16.5 | 7.46 |
| Example 2 | 1.4 | 5.1 | 47.8 | 15 |
| Example 3 | 3.7 | 24.7 | 79.7 | 34.9 |
| Example 4 | 8.1 | 31.3 | 76 | 42.9 |
| Example 5 | 4.8 | 20.8 | 61.3 | 28.2 |

As is seen from Table 3, it was seen that the particle size became smaller as the pressure of the high pressure homogenizer increased (Examples 1, 2 and 3).

In addition, it was seen that the particle size became rather uniform as the preparation volume increased (Examples 4 and 5). It is considered that this is due to a decrease in non-uniformity of the particles generated at the beginning and the end portions as the time taken for microsphere preparation decreases.

Figure 2A:
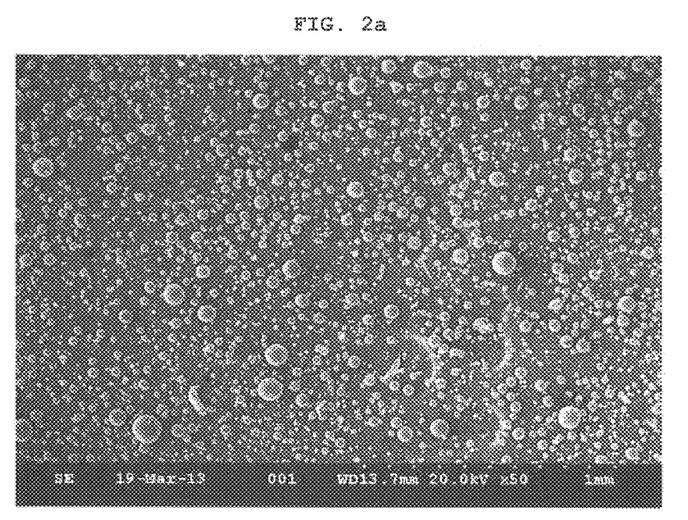
FIGS. 2a and 2b is a scanning electron microscope (SEM) picture of the surface of microspheres prepared according to Examples 4 and 5. Herein.
Figure 2B:
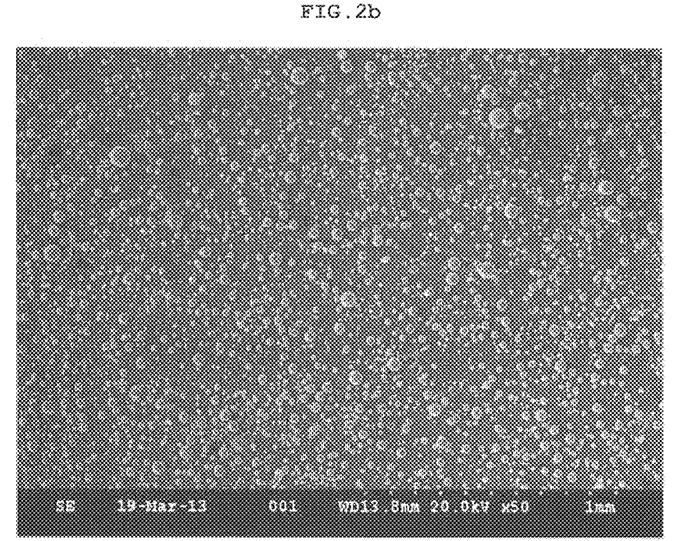

Experimental Example 3: Measurement of Leuprolide Acetate-Containing Microsphere Surface Morphology The surface of the microspheres prepared using the methods of Examples 4 and 5 was observed using a scanning electron microscopy (SEM), and the measurement results are shown in FIG. 2a and FIG. 2b.

When compared to Example 4, Example 5 had preparation scale increase of 10 times, however, in Example 5, the particle size was observed to be rather uniform and small. When a preparation scale increases 10 times in a typical discontinuous process, the energy for dispersion needs to be proportionally increased when forming a second emulsion. The form of the energy may include a method of increasing the rpm of a homogenizer, using ultrasonic waves, homogenizing the whole solution using an in-line homogenizer while rotating the whole solution, and the like. The preparation volume also needs to be increased in proportion to the preparation scale, and the reason is that the volume of a second solution with respect to a first emulsion greatly affects the encapsulated amount. In order to maintain at least the same encapsulated amount, the volume of the second solution needs to be proportionally increased as the preparation scale of the first emulsion increases. As a result, the preparation volume increases with the preparation scale, and particles with the same size are obtained only when high energy is applied for dispersion. The present invention adopts a method in which constant volumes and amounts of fine particles are continuously prepared regardless of the preparation scale and the preparation volume thereby has an advantage in that the particles are formed rather uniformly as the preparation scale increases. In addition, separate physical conditions need to not be changed even when the preparation scale increases.

What is claimed is:

1. A process for preparing microspheres in which a physiologically active substance is encapsulated in a carrier polymer using a double emulsification method, comprising:
   dispersing or mixing a carrier polymer dissolved in a solvent and a physiologically active substance to form a first emulsion (Step 1);
   continuously mixing a certain amount of each of the first emulsion and a second solution in which a surfactant is dissolved to form a second emulsion (Step 2); and
   continuously flowing the second emulsion through a high pressure homogenizer or a high pressure pump and applying pressure of 500 psi to 30,000 psi to the second emulsion before the polymer is cured as the solvent in the first emulsion is evaporated or removed, thereby controlling the size of microspheres before the polymer is cured as the solvent in the first emulsion is evaporated or removed (Step 3).

2. The process of claim 1, further comprising the step of: stirring the second emulsion (Step 4) after the Step 3.

3. The process of claim 1, wherein Step 2 is performed by continuously transferring a certain amount of each of the first emulsion and the second solution into a reactor, in which the second emulsion is formed, by a liquid transfer pump, and by mixing the first emulsion and the second solution to form the second emulsion.

4. The process of claim 3, wherein the reactor has a mesh net installed on the inside, and the second emulsion is formed after the first emulsion and the second solution pass through the mesh net.

5. The process of claim 4, wherein the mesh net has a pore size ranging from 1 µm to 50 µm.

6. The process of claim 2, wherein the Step 4 is performed by continuously injecting the second emulsion from a reactor, in which the second emulsion is formed, into an agitator, and stirring the second emulsion in the agitator.

7. The process of claim 6, wherein the rate of injecting the second emulsion into the agitator is the same as the rate of supplying the first emulsion and the second solution to the reactor.

8. The process of claim 6, wherein a means to inject the second emulsion into the agitator includes a high pressure pump or a liquid transfer pump.

9. The process of claim 1, wherein the physiologically active substance is any one or more selected from the group consisting of a luteinizing hormone-release hormone (LHRH) homologue, a peptide, and salts thereof.

10. The process of claim 9, wherein the physiologically active substance is any one or more selected from the group consisting of goserelin, leuprolide acetate, triptorelin, buserelin, nafarelin, cetrorelix and argitide.

11. The process of claim 1, wherein the carrier polymer is a biodegradable polymer.

12. The process of claim 11, wherein the carrier polymer is one or more selected from the group consisting of polylactide, polyglycolide, and poly(lactide-co-glycolide), polyorthoester, polyanhydride, polyamino acid, polyhydroxybutyric acid, polycaprolactone, polyalkyl carbonate, lipid, fatty acid, wax, albumin, gelatin, collagen, fibric acid, alginic acid, chitin, chitosan, dextran, hyaluronic acid and starch.

* * * * *